United States Patent [19]
Carlsen et al.

[11] Patent Number: 5,450,193
[45] Date of Patent: Sep. 12, 1995

[54] RAMAN SPECTROSCOPY OF AIRWAY GASES

[75] Inventors: William F. Carlsen, Woodside; Tad D. Simons, Palo Alto; Richard J. Pittaro, San Carlos; Jeffrey Perry, Cupertino; George W. Hopkins, II, Sunnyvale; Damien F. Gray, Mountain View, all of Calif.

[73] Assignee: Hewlett-Packard Company, Palo Alto, Calif.

[21] Appl. No.: 226,245

[22] Filed: Apr. 11, 1994

Related U.S. Application Data

[63] Continuation of Ser. No. 840,436, Feb. 24, 1992, abandoned.

[51] Int. Cl.⁶ .................................................. G01J 3/44
[52] U.S. Cl. ...................................... 356/301; 356/246
[58] Field of Search .................................. 356/301, 246

[56] References Cited

U.S. PATENT DOCUMENTS

| | | |
|---|---|---|
| 3,406,289 | 10/1968 | Schleusener . |
| 3,414,354 | 12/1968 | Siegler, Jr. . |
| 3,556,659 | 1/1971 | Hawes . |
| 3,704,951 | 12/1972 | Chupp ........................ 356/75 |
| 3,723,007 | 3/1973 | Leonard ...................... 356/75 |
| 3,766,489 | 10/1973 | Rosenberg et al. . |
| 3,951,526 | 4/1976 | Grossman . |
| 4,127,329 | 11/1978 | Chang et al. ............... 356/301 |
| 4,212,539 | 7/1980 | Berber et al. ............... 356/336 |
| 4,410,271 | 10/1983 | Matthews ................... 356/301 |
| 4,571,079 | 2/1986 | Knollenberg ............... 356/336 |
| 4,630,923 | 12/1986 | Tans ............................ 356/301 |
| 4,645,340 | 2/1987 | Graham et al. ............. 356/301 |
| 4,648,714 | 3/1987 | Benner et al. .............. 356/301 |
| 4,676,639 | 6/1987 | Van Wagenen ............ 356/246 |
| 4,784,486 | 11/1988 | Van Wagenen ............ 356/301 |
| 4,818,882 | 4/1989 | Nexo et al. .................. 356/343 |
| 5,121,988 | 6/1992 | Blesener et al. ............ 356/442 |

FOREIGN PATENT DOCUMENTS

| | | |
|---|---|---|
| 1291535 | 10/1965 | Germany . |
| 1900885 | 1/1969 | Germany . |
| 2723939 | 7/1978 | Germany . |
| 1124126 | 3/1966 | United Kingdom . |
| 1171689 | 4/1967 | United Kingdom . |
| 2241080 | 8/1991 | United Kingdom . |
| WO88/06725 | 2/1988 | WIPO . |

OTHER PUBLICATIONS

Schwab, S. B. & R. L. McCreery, "Remote, Long-Path Length Cell for High Sensitivity Raman Spectroscopy," Applied Spectroscopy, vol. 41, No. 1, 1987, pp. 126–130.

E. P. Ippen, "Low-Power Quasi-cw Raman Oscillator", Apr. 15, 1970, Applied Physics Letters, vol. 16, No. 8, pp. 303–305.

G. E. Walrafen et al., "Intensification of Spontaneous Raman Spectra by Use of Liquid core Optical Fibers", Nov. 6, 1972, Applied Spectroscopy, vol. 26, No. 6, pp. 585–589.

H. B. Ross, "Liquid Core Optical Fibers In raman Spectroscopy", 1981, Applied Spectroscopy, vol. 35, No. 4, pp. 439–442.

(List continued on next page.)

Primary Examiner—Vincent P. McGraw
Assistant Examiner—K. P. Hantis

[57] ABSTRACT

Method and apparatus for determining the composition and concentration of gases present in a patient's airway by measurement of the spectrum of Raman scattered light from these gases. The efficiency is improved by collecting Raman scattered light generated outside the collection region. The gases present are assumed to be drawn from a predetermined set of gases with known Raman scattering spectra, and the concentrations are determined by solution of a matrix equation $Ac=b$, where the c vector components are the unknown concentrations and the b vector components are determined from measurements of the Raman scattering intensifies in a plurality of wavelength or wavenumber intervals. The linear system of equations represented by the matrix equation may be overdetermined and may require solution by non-conventional methods, such as singular value decomposition.

6 Claims, 7 Drawing Sheets

OTHER PUBLICATIONS

S. D. Schwab et al., "Versatile, Efficient Raman sampling With Fiber Optics", Anal. Chem., 1984, pp. 2199–2204.

S. D. Schwab et al., "Remote, Long-Pathlength Cell for High-Sensitivity Raman Spectroscopy", Applied Spectroscopy, vol. 41, No. 1, 1987, pp. 126–130.

A. Weber et al., "High-Resolution Raman Spectroscopy of Gases with cw-Laser Excitation", Journal of the Optical Society of America, vol. 57, No. 1, Jan. 1967.

M. Hercher et al., "An Efficient Intracavity Laserr Raman Spectrometer", Applied Spectroscopy, vol. 32, No. 3, 1978, pp. 298–302.

English Translation of Ref. doc. DE2723939.

RAMAN SPECTROSCOPY OF AIRWAY GASES

CROSS REFERENCE TO RELATED APPLICATION

This is a continuation of copending application Ser. No. 07/840,436 filed on Feb. 24, 1992, now abandoned.

FIELD OF THE INVENTION

This invention relates to determining the composition and concentration of an arbitrary mixture of gases in a patient's airway, and more particularly to such determination by means of Raman spectroscopy.

BACKGROUND OF THE INVENTION

Measurement of the composition of a gas mixture is especially important in the airway of an individual who is connected to an auxilliary breathing apparatus. Examples include ventilators which assist respiration in the intensive care unit and coronary care unit in hospitals, and anesthesia machines in hospital operating rooms ("ORs"). These patients are often monitored closely for their vital signs, including respiratory gas exchange.

In the operating room, the anesthesiologist supports the patient's respiration and also controls the patient's depth of anesthesia using special gaseous agents. A patient airway will contain the normal respiratory gases, such as oxygen ($O_2$), carbon dioxide ($CO_2$), and water vapor ($H_2O$), or a mixture of nitrous oxide ($N_2O$) and one or more halogenated anesthetic agents ("HA", usually halothane, enflurane, isoflurane, desflurane or sevoflurane). Occasionally, nitrogen ($N_2$) from room air infiltrates the system. Various metabolic products and special gases, for example, to measure pulmonary function, may also be present. Also, interferences from extraneously introduced gases such as ethanol and isopropanol may be present. Because severe injury can result from use of an improper gas mixture, anesthesiologists prefer to measure the composition of the patient breathing mixture. Every component of the mixture is important. Measurement of oxygen concentration helps prevent hypoxia. Presence of the $CO_2$ waveform indicates healthy gas exchange. Measurement of the type and concentration of the various anesthetic agents helps control and adjust the proper depth of anesthesia. The presence of other gases can indicate leaks and possible system malfunctions.

Several Anesthesia Monitors ("AMs") exist today that perform this function. Four different technologies compete for most of the market today.

(1) Infrared Absorption plus Oxygen. One class of AMs uses infrared absorption to measure the halogenated anesthetics, $CO_2$, and $N_2O$. While this technique is widely used, it has the disadvantages that it is difficult to distinguish the HAs from each other, because they have similar IR spectra that must be measured in the region $\lambda = 3-4$ $\mu m$. Identification of the individual agents requires measurement in the far infrared region, $\lambda > 10$ $\mu m$, which is more difficult. A separate measurement, using a paramagnetic or polarographic sensor, is needed to measure $O_2$, which has no infrared ("IR") spectrum. Also, separate cells are needed to measure the HAs and the $CO_2 + N_2O$ concentrations. In addition, these devices have no means to detect other gases which may be present. Such devices may introduce error in the measurements, and the devices cannot be adapted easily to measure new agents.

(2) Mass Spectrometry. Mass spectrometers ("MS") can provide extremely accurate measurements of gas concentrations. Historically, MS devices are expensive and complicated instruments that require frequent calibration and maintenance. These devices require use of a delicate vacuum system and ion source. Typically, many operating rooms share a single MS. This reduces the response time between measurements, and requires relatively long sampling lines, which can distort the gas samples. In addition, the mass spectra of the various OR gases are not unique. Nitrous oxide and carbon dioxide have the same mass number, and isoflurane and enflurane are isomers. Therefore, one must observe fragmentation of these molecules in the system and employ special algorithms to distinguish the molecules. The systems must also be protected from some other gases, including helium and water vapor. Shared systems cannot provide continuous, breath-to-breath analysis of airway concentrations, which is desirable. At least one manufacturer has introduced a small, stand-alone MS, offering each OR suite a dedicated measuring device. Although this device eliminates the problem of multiplexing measurements for different users, and has a more convenient design, the device still requires protection from contaminants, and can only be configured to measure a few specific gases at a time. The problems of high cost and distinguishing between isomers and between identical mass spectra remain.

(3) Photo-acoustic Spectroscopy. These devices also utilize the properties of infrared absorption to characterize gas mixtures. A precision microphone detects pressure waves which are produced when the gas sample absorbs IR energy. The sound level indicates the concentration. Like the IR systems described above, these devices need a separate system to measure oxygen concentration, and the technique cannot easily distinguish different HAs from each other.

(4) Raman Spectroscopy. Scattering of light by the Raman effect has received much attention from scientists since its original exposition by C. V. Raman in 1928. Simply stated, when monochromatic light illuminates a vibrating molecule, light scatters in a process which decreases or increases the frequency of the scattered light by exactly the vibrational frequency of the molecule. The shift in frequency of radiation is characteristic of the scattering medium, and is independent of the frequency of the illuminating radiation. Thus, measurement of the Raman-scattered light can be used to infer the properties of the medium, such as the chemical composition and concentration. For measurements of OR and airway gases, this technique has the advantage that each OR gas, including oxygen and any polyatomic molecule, has a unique Raman spectrum. Additionally, the Raman spectrum for a gas is usually contained in a relatively narrow wavelength band, which simplifies detection. Thus, Raman spectroscopy offers the promise of simultaneous measurement of all airway gases with a single measurement and less complex technology.

In Raman scattering, a small fraction of collisions of photons with an atom or molecule are inelastic, with a photon either giving up a small portion of its initial energy $E_0$ to the collision partner and scattering as a photon of reduced energy $E < E_0$ (Stokes waves) or the collision partner giving up a small portion of its initial energy so that the photon scatters with increased energy $E > E_0$ (anti-Stokes waves). In Rayleigh scattering of a photon with an atom or molecule, by contrast, the energy of the scattered photon is equal to the initial energy of the photon. This does not include light that is absorbed and re-emitted by processes such as phosphorescence or fluorescence. In a typical scattering situation, the ratio of intensity of Rayleigh to initial light intensity for gases might be about $10^{-9}$ and the ratio of intensity of Raman scattered light to initial light intensity might be about $10^{-12}$. The change in wavelength for a Raman scattered photon of initial wavelength $\lambda_0 = c/f_0$ and scattered light wavelength $\lambda_R = c/f_R$ is given by $$\Delta\lambda = \lambda_R - \lambda_0 = (c/f_R) - (c/f_0), \quad (1)$$

where $\Delta\lambda > 0 (\Delta\lambda < 0)$ corresponds to appearance of Stokes waves (anti-Stokes waves). Substantially all scattered light at moderate initial energies arises from Rayleigh scattering or Raman scattering. For molecules of moderate or higher symmetry, not all modes of molecular vibration result in Raman lines. Some of the modes of molecular vibration produce infrared absorption lines but not Raman scattering lines, some modes produce Raman lines but not infrared lines, some modes produce both Raman and infrared lines, and some vibration modes produce neither Raman nor infrared lines.

The Raman scattering cross-sections are extremely small, and the intensity of the scattered light is very weak, as noted above, especially in gases where the molecular number density is also relatively small (compared to liquids and solids), and are therefore difficult to measure with accuracy. The differential intensity of the Raman-scattered light scattered into a differential solid angle $d\Omega$ along a differential path length $dz$ in a single component gas is given by the formula $$dP_{Raman} = P_0 n_0 (d\sigma/d\Omega) d\Omega dz, \quad (2)$$

where $P_o$ is the intensity of the incident light, $n_o$ is the number density of the scattering molecules, and $(d\sigma/d\Omega)$ is the differential scattering cross-section in a given direction. The direction of the scattering is also dependent on the polarization of the incident light. If the gas contains more than one component and the components do not interact appreciably with one another, the intensity of each Raman line of a gas component is proportional to the concentration of that component so that Equation (2) above can be used with a small modification to take account of the presence of the other components.

For a given intensity of the incident radiation and sample concentration, one can maximize the magnitude of the measured Raman signal only by increasing the solid angle of the light-collecting optics, or by increasing the observation path length (i.e., using a larger scattering volume), because the molecular properties of the sample are not variable.

In a conventional system for observing Raman-scattered light, a laser beam is brought to a focus in the medium of interest, creating a minute region of relatively intense electrical field, which excites the Raman effect. The light scattered from this region is collected by an optical system, typically a simple lens which images the scattering region onto a suitable optical filter and detector. The difficulty of improving this simple design is evident from the observation that the etendue (defined as the product of the collection area and collection solid angle) is conserved in any ideal optical system. Thus, increasing the solid angle of light collection (lower f number optics) decreases the observable area (and thus the path length). Each experimental system must optimize these parameters against its own constraints. Some Raman systems further improve signal intensity by providing multiple passes of the incident light beam through the observation volume, effectively increasing the path length, or by placing the observation volume inside an optically resonant cavity, effectively increasing the incident intensity $P_o$.

Analysis of Raman scattered light is especially useful where the Raman spectrum of each of the components present in a sample is a relatively simple line pattern and the Raman lines of the different components do not coincide with or lie close to one another. A complete range of vibrational frequencies can be covered with one monitoring instrument, and the sample container can be glass or many other relatively transparent materials. Water may be present; the Raman spectrum of water is weak and diffuse in the band 200-3300 cm$^{-1}$, but the spectrum has a strong, broad peak centered at 3652 cm$^{-1}$. The approximately linear relationship between component concentration and Raman-scattered light intensity makes the calculation of concentration straightforward. Integration across a portion of the Raman spectrum to determine the intensity of specified lines is also straightforward. However, the sample should be non-fluorescent, and the sample to be analyzed should be relatively transparent, with little or no absorption at the wavelengths of interest, and should be free of particulates. It is often difficult to apply Raman scattering to very low concentrations of the sample, because of the weak intensity of the individual Raman lines.

Raman systems that measure the composition in patient airways must measure multiple spectral lines in order to distinguish all the component gases. Several earlier patents describe techniques for measuring multiple gases.

Albrecht, in German Pat. DE 2723939C2, describes a system of six detectors mounted in an equatorial plane around a region of focus. The focal region has a confocal cavity where the exciting laser beam makes multiple passes through the sample. This system requires six different detection channels, each with associated collection optics, laser line rejection and Raman line filters, and separate detector. The configuration is limited to six channels and uses an unpolarized laser beam. More channels would be needed to measure all the OR gases of interest. In addition, the confocal cavity and each of the collection optics requires delicate adjustment to assure proper imaging of the focal region onto the detectors.

In U.S. Pat. No. 3,704,951, Chupp discloses use of a multi-pass gas cell for increasing the intensity level of light that is Raman scattered from a gas sample contained in the cell. Raman scattered light exits from the cell through a large side window in the cell.

Leonard, in U.S. Pat. No. 3,723,007, discloses a gas cell with a transparent side window for Raman scattering analysis and notes that two or more simple molecular gases may have distinct Raman shift spectra.

A spectrophotometer that compares light Ramnan scattered from a known gas sample with light Raman scattered from an unknown gas sample is disclosed by Tans et al in U.S. Pat. No. 4,630,923. Raman scattered light from the known and unknown gas samples is alternatingly received by a detector to determine the concentration ratios of two gases present in the unknown gas sample.

A gas monitoring system, disclosed by Benner et al in U.S. Pat. No. 4,648,714, collects light from a single focal region, illuminated by a properly oriented, polarized laser beam. A single set of collection optics images the scattered light onto a single detector. An additional mirror, placed opposite the collection optics, reflects Raman-scattered light back into the focal region and into the collection optics, further enhancing the signal. The sample cell can be inside the resonant cavity of the exciting laser to increase the signal still more. The system employs a rotating filter wheel that passes different Raman line filters in front of the detector so that different Raman lines are measured sequentially. While this system can measure a larger number of Raman spectral lines (by adding more filters), the samples are not acquired simultaneously from the same gas sample. This reduces the ability of the system to respond rapidly, as is desired for breath-by-breath analysis of the airway composition.

In U.S. Pat. No. 4,676,639, Van Wagenen discloses use of a gas cell for Raman scattering analysis with transparent end and side windows. The side windows may be coated with a narrow band anti-reflection coating, for passage of the Raman scattered light for detection outside the gas cell.

Van Wagenen et al describe another system in U.S. Pat. No. 4,784,486, which uses multiple detection units, each including collection optics (lens and back reflector), laser line rejection and Raman line filters, and a detector. Each detection unit collects Raman-scattered light simultaneously from separate focal regions. The system is similar to the system of Bennet, but employs a completely separate detection unit for each Raman line, rather than inserting different filters serially. This design has the advantage that all the channels can acquire measurements simultaneously. However, the measurements are generated from different sample volumes and, thus, from different gas molecules. The sample gas must flow from location to location, and the flow rate must be such that all units see a mixture of substantially similar composition. Thus, for a given flow rate and size of sample cell, the practical number of detector units is limited by the desired time response of each system. This creates limitations because it is desirable to sample as small a volume as possible from the patient airway. An increase in the number of detection units increases the expense of the unit proportionally. Each unit also requires separate alignment and adjustment, which increases the complexity and cost of the system.

Many of the systems discussed above employ a combination of individual narrow-band filters. Each individual filter examines only a single spectral line or a small spectral region. This requires that a system use at least one filter for every molecule spectral peak of interest. Allowing for the expense of multiple channels and filters, these systems are suited to the measurement of gas mixtures, where the Raman spectrum of each gas consists of a single peak or a few well-separated peaks, and where these spectral peaks are unique for each gas in the mixture, with no overlapping spectral lines. In this case, each filter can measure each gas separately and completely. Overlapping spectral lines can be ignored if the gas of interest has another unique peak. This is true for the gases $N_2$, $O_2$, $CO_2$, and $N_2O$. The principal spectral lines of these gases are listed below as frequency shifts from the frequency of the illuminating source, such as a laser beam. Note that $CO_2$ and $N_2O$ have an overlapping line at 1285 $cm^{-1}$.

$N_2$, nitrogen: 2331 $cm^{-1}$
$O_2$, oxygen: 1555 $cm^{-1}$
$CO_2$, carbon dioxide: 1285 and 1388 $cm^{-1}$
$N_2O$, nitrous oxide: 1285 and 2224 $cm^{-1}$ The limitations of these types of systems, which employ separate filters, arise when the Raman spectra of one molecule of interest becomes complicated, when it covers a larger spectral band or has many, scattered peaks, such as the halogenated anesthetics. These spectra are best characterized by their entire spectrum, not by single lines. The Raman spectra from the HAs have considerable spectral overlap with each other, and the broadband emission can contribute error to the signals of the respiratory gases and $N_2O$. A representative mixture of the respiratory and anesthetic gases produces a complicated signal, with emissions and spectral lines across the entire spectrum, a mixture of all the individual spectra. Measurement of single spectral lines therefore gathers less signal and less information than a technique that gathers the entire spectral signature of the mixture or of a single component. Single filter systems use only small amounts of the total signal available, because such systems measure only part of the Raman emissions. For the HAs, measurement of a single line neglects most of the total signal. Single filter systems also neglect significant information about the Raman spectra. It is much easier to distinguish each HA from examination of its entire spectrum than from a single, possibly weak, line.

A further limitation of the single filter system is that new or additional gases cannot be measured without the addition of new detection units with new filters. New gases which have substantial spectral overlap with existing gases may be very difficult to measure, even with additional filters.

Also, if a Raman spectrum has closely spaced lines that must be distinguished from each other, the spectral bandwidth of the individual filters must be sufficiently narrow to differentiate nearby lines, or obscure undesired lines. This places a constraint on the spectral bandwidth of the laser source, which must be at least as narrow as the Raman line filters, and the laser must not drift in wavelength. This constraint also reduces the detected power. Further, filters can drift as they age. If a filter has a bandwidth of 1 nm, and the laser drifts in wavelength from 800 nm to 803 nm, the Raman line of interest moves out of the band of the filter and is not measurable. For these reasons, existing filter-based Raman systems often use gas lasers, such as argon-ion, which has narrow, constant lines and requires high input power. Solid-state lasers have wider line widths ($>1$ nm), and often require special wavelength stabilization. Semiconductor lasers presently require low input power and produce wider linewidths.

What is needed is a gas monitoring system that (1) allows simultaneous determination of the concentration of components in a multiple component gas; (2) is very efficient and uses as much of the total signal available as possible for examination of the spectrum; (3) allows interrogation of a broad spectrum in a single measurement of a small single sample; (4) allows distinctions to be made relatively easily between gas components that may be present; (5) allows considerable freedom in the choice of sample container and sample concentration; (6) allows the system to monitor and identify different compounds with minimal system modifications; and (7)

allows use of low power light sources and of relatively low cost detectors.

SUMMARY OF THE INVENTION

These needs are met by the invention, which provides in one embodiment, a light beam of a selected wavelength $\lambda_0$, chosen to promote Raman scattering in at least one of a predetermined group of gases that may be present in the patient's airway; and a sample cell to receive and temporarily hold gas from a patient's airway, the cell being relatively transparent along the beam axis to light of wavelength $\lambda_0$ and being positioned to receive the light beam so that gas in the sample cell is illuminated by the light beam. The invention also provides spectrograph means, having a beam entrance and wavelength dispersion means, for receiving a scattered light beam at the beam entrance, for directing the scattered-and-received light beam to the wavelength dispersion means for dispersing this light beam into a plurality of light rays, each ray having a different interval of light wavelengths. Light collection means is also provided, for collecting portions of the light beam that undergo Raman scattering by one or more of the gases in the sample cell and for directing these portions of the light beam to the spectrograph means beam entrance. The invention further provides an array of photodetectors, each of which receives one of the plurality of wavelength-dispersed light rays from the spectrograph means and issues a photodetector output signal representing the amount of Raman scattered light received by that photodetector. Finally, the invention provides computation means for receiving the photodetector output signal from each of M photodetectors (M > number of gases to be tested for) and for computing the relative or absolute amount of Raman scattered light received by each such photodetector.

This invention measures the complete Raman spectrum of a gas mixture to determine its composition. The invention gathers information about all the gases present simultaneously, and from a single, small sample volume. Further, the invention will combine techniques of light collection, spectral separation, and signal processing to maximize the total amount of light collected by the spectrometer, and to utilize the information contained in the entire Raman spectrum to predict more accurately the composition of the mixture. It is also the intention of this invention to provide a means whereby new or additional gases can be detected in the airway gas mixture, without altering the basic spectrometer, sample cell or structure of the algorithm used.

The invention is an efficient means for collecting the optical signals generated by Raman scattering of an optical beam in gases.

The Basic Invention Consists of the Following Essential Components

1. A monochromatic source of illumination, e.g., a laser;
2. A means of sampling and containing the gaseous media;
3. A system of collection optics;
4. A wavelength-selective filter to distinguish the Raman signals;
5. A photodetector; and
6. Computation means to determine gas composition from photodetector signals.

Earlier inventors have avoided using a grating spectrometer as a wavelength-selective filter because of high cost and low optical efficiency. The invention described here combines several new ideas and technologies that reduce these limitations. Traditionally, grating spectrometers are used to observe the molecular structure of compounds. These systems are often optimized for high resolution, and have low optical throughput—a narrow entrance slit and "slow" optics. These spectrometers are often designed to observe a wide range of compounds, whose structure or spectra are often unknown.

In contrast, this invention employs a grating spectrometer to measure the concentration, not molecular structure, of a limited number of known compounds, such as the airway gases. This invention takes advantage of these differences to optimize the combination of spectrometer optics, unconventional entrance slits, and diode array elements for the determination of airway gas concentrations. The optimized optical system, in further combination with an intensified source of Raman-scattered light, and an optimized data reduction technique, are part of the present invention. Key elements of the new invention are use of 1) a means to maximize the intensity of Raman-scattered light from a small aperture, 2) a large etendue for the spectrometer, and 3) an optimized data reduction means to determine concentrations.

DESCRIPTION OF BEST MODE OF THE INVENTION

Figure 1:
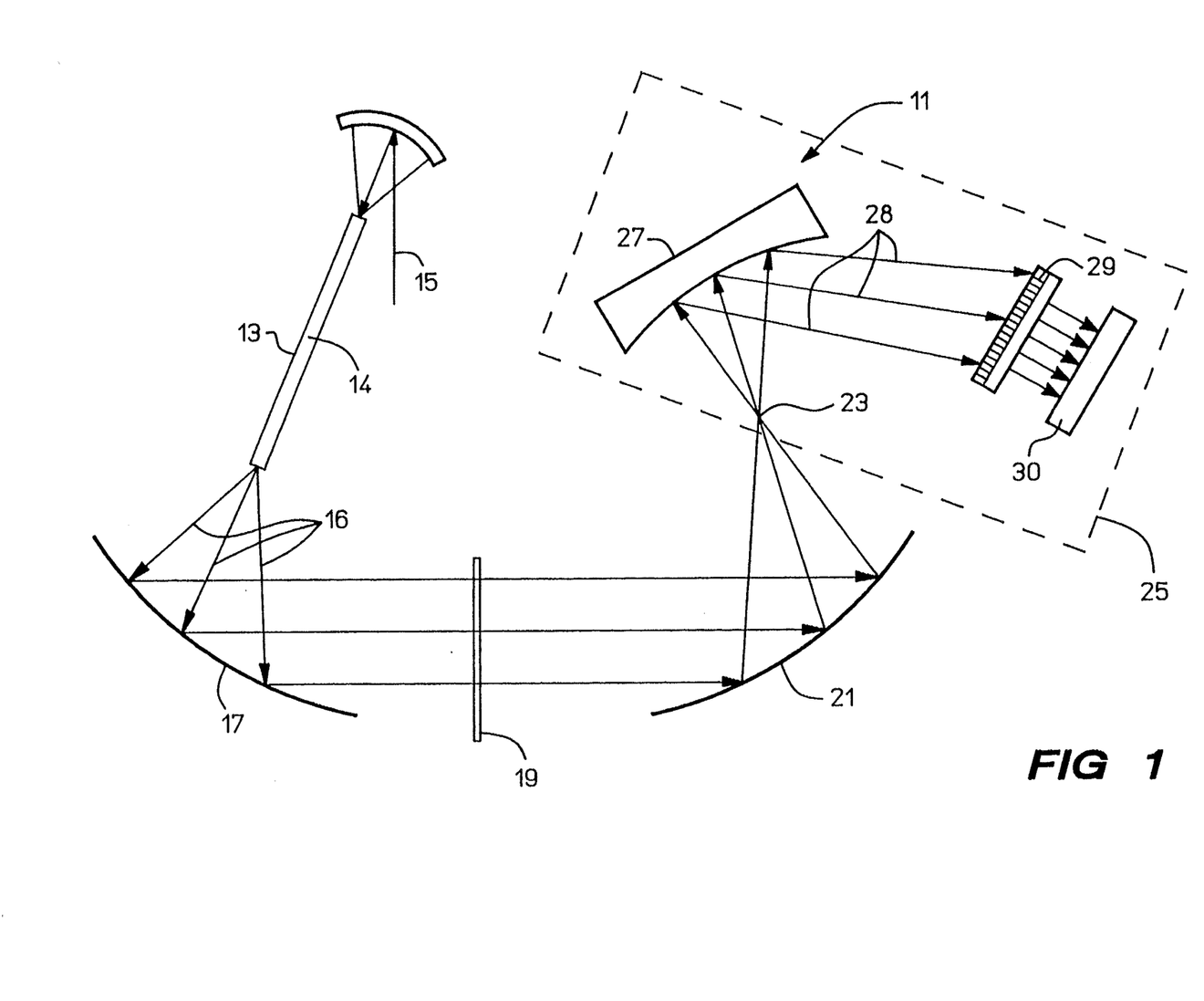
FIG. 1 is a schematic view of one embodiment of the invention.

A preferred embodiment 11, shown in FIG. 1, includes an optical waveguide 13, through which a gas sample 14 flows. A laser beam 15 passes along the longitudinal axis of the waveguide 13 and produces Raman scattering along the entire waveguide length. The laser beam 15 is preferably directed through the waveguide 13 to minimize diffuse scattering of the laser beam from the interior surfaces of the waveguide, but this is not essential. The laser that produces the laser beam 15 may be a gas laser, such as He-Ne or argon-ion, but is preferably a solid-state laser diode emitting visible or near-infrared light in the wavelength range $\lambda = 500$–$850$ nm. One embodiment of the waveguide 13 is described in a co-pending patent application by Carlsen et al, "System for Collecting Weakly Scattered Electromagnetic Radiation", U.S. Ser. No. 07/840,108 filed Feb. 24, 1993, and assigned to the assignee of this invention. A preferred embodiment of the waveguide 13 is a cylindrical tube whose internal surfaces are substantially fully reflective at the Raman shifted wavelengths of interest, for example a smooth silver-plated surface approximately 100 mm long with inside diameter between 1 and 2 mm. In this manner, the effective length of interaction (dz in Equation (2)) is increased substantially, thereby increasing the total Raman signal. In another preferred embodiment, the laser beam propagates in an optically resonant cavity that is surrounded by the waveguide 13.

The scattered light is trapped in the waveguide or tube 13 and emits from each end of the waveguide in the same manner as that light emits from a solid optical fiber. The small diameter of the tube 13 provides a small aperture for imaging the Raman light 16 by the collection optics. The collection optics preferably includes a lens 17 whose focal point is positioned near the aperture of the waveguide and that has an aperture with f number approximately equal to 1. The lens 17 substantially collimates the beam of Raman light and directs the beam through a laser line rejection filter 19 that blocks any scattered radiation at the wavelength of the laser beam 15. A second lens 21, also part of the collection optics, images the Raman light 16 through the entrance slit 23 of a spectrometer 25. The spectrometer optics may also contain other elements that produce sharp slit patterns at the location of the spectrometer slit 23. The preferred embodiment has only one slit 23 at the entrance to the spectrometer 25. However, multiple slits, with different widths and spacings, may be used to increase the illumination inside the spectrometer 25.

The spectrometer 25 preferably includes a diffraction grating spectrometer 27. Raman-scattered light from the slit(s) 23 is directed at a concave diffraction grating 27, which is preferably a holographic element or replica that is produced for high efficiency diffraction in the wave number range of interest (approximately 200 $cm^{-1}$ to 3300 $cm^{-1}$ shift from the laser beam wave number). Use of replicas or masters of a holographic grating to disperse and image the Raman light reduces the system cost and system parts count, while providing very good performance. The grating 27 disperses the Raman-shifted light 28, which contains all the Raman shift frequencies from all the spectral lines from the gas mixture, across the elements of a photosensor array 29.

The photosensor array 29 is preferably a silicon photodiode array of approximately 56 elements, but can be a larger or smaller array of pin photodiodes, or a CCD array. Each element of the array 29 corresponds to a single, narrow wavelength band of light. Thus, the photosensor array 29 measures the entire spectrum of Raman scattering from the mixture simultaneously. The amount of light incident on each element of the array 29 is proportional to the amount of Raman scattering in that wavelength band and is received by computation means 30 that determines relative or absolute concentrations of the gases 14.

Figure 2:
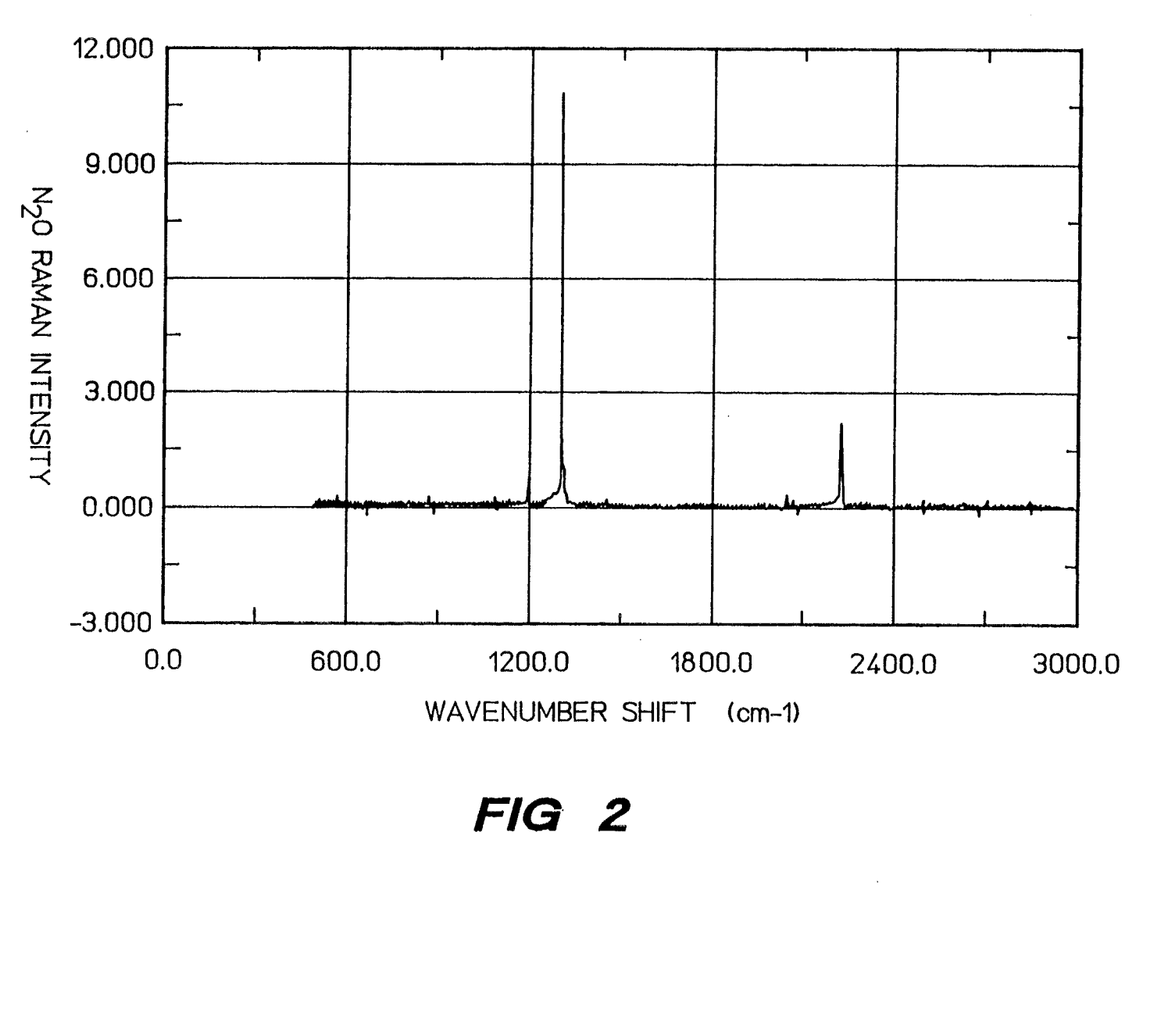
FIGS. 2 and 3 are graphical views of the Raman scattering spectra for two gases, $N_2O$ and $CO_2$, that are likely to be present in a patient's airway.
Figure 3:
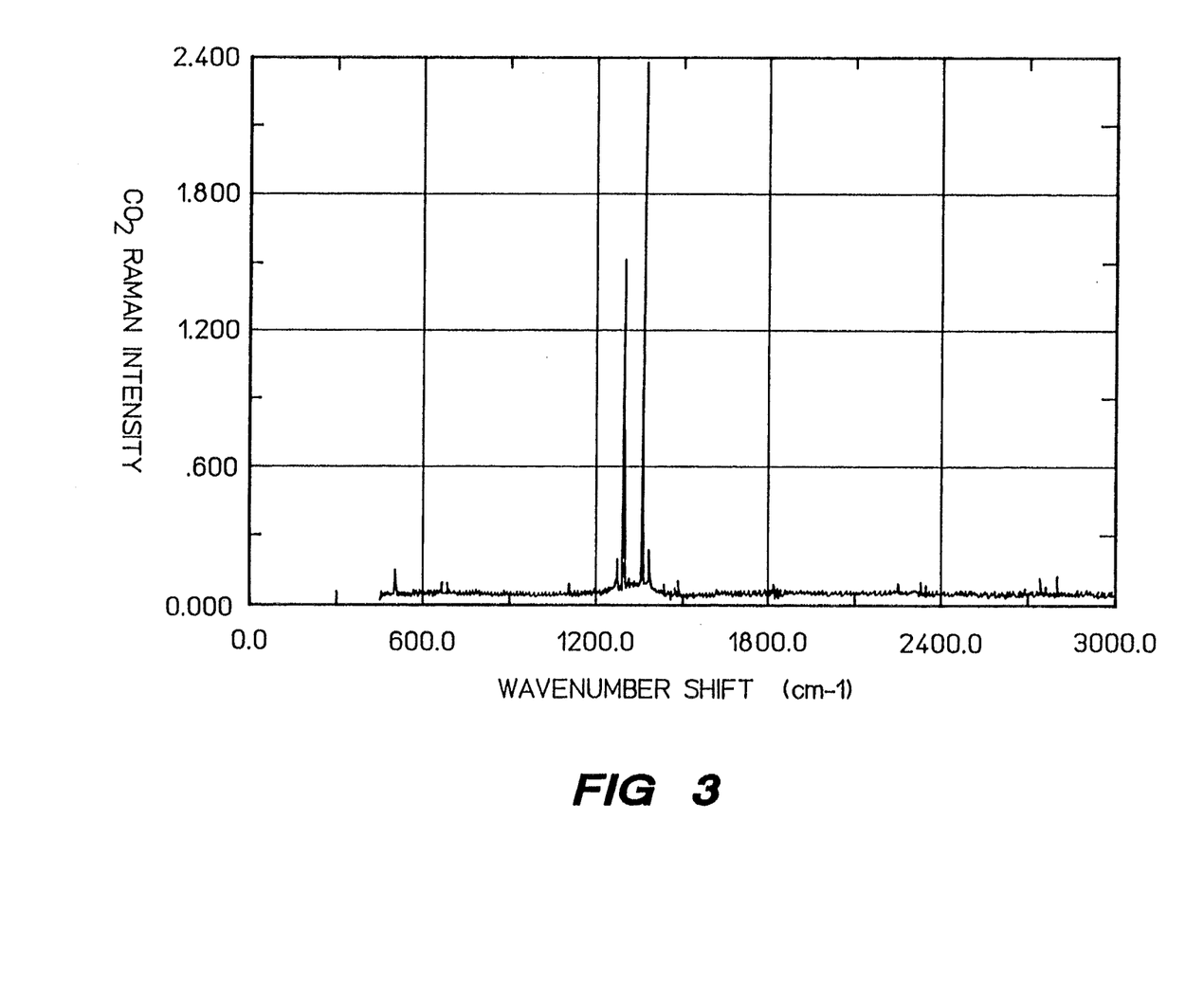

The composition of the gas mixture can be determined by analyzing the measured spectrum, which represents the sum of the spectra of the individual gases, weighted by the concentration of each gaseous component. For illustrative purposes, the Raman scattering spectra for the gases $N_2O$ and $CO_2$ are shown in FIGS. 2 and 3, respectively, as a function of wavenumber shift $\Delta \nu^1 = \nu_0^1 - \nu_R^1$ over the range $0\ cm^{-1} \leq \Delta \nu^1 \leq 3{,}000\ cm^{-1}$ for Stokes waves. Each gas of interest may have one or several prominent spectral lines, and a prominent line of one gas may be adjacent to a prominent line of another gas. Other airway gases of interest include $N_2$, $O_2$, $SF_6$, halothane ($CF_3$—$CHClBr$), enflurane ($CHClF$—$CF_2$—$O$—$CHF_2$), isoflurane ($CF_3$—$CHCl$—$O$—$CHF_2$), desflurane ($CF_3$—$CHF$—$O$—$CHF_2$), sevoflurane ($CH(CF_3)_2O$—$CH_2F$), methoxylflurane ($CH_3$—$O$—$CF_2$—$CHCl_2$), ethanol ($C_2H_5OH$), isopropanol ($C_3H_7OH$), ether, cyclopropane, acetone ($O$=$C(CH_3)_2$) and water vapor.

Because the photosensor array 29 has substantially more elements than the number of component gases, there exists a surplus of information from which to determine the concentrations: The solution is overdetermined. Mathematically, one seeks the optimal solution vector c to the system of equations $Ac = b$, where A is a design matrix of the basis functions representing spectra of each individual gas, c is a vector representing the unknown concentrations of each gas in the mixture, and b is a vector representing the measured spectrum from the diode array. The vector components b in the linear system of equations $Ac = b$ serve as a forcing function whose values are determined by experimental measurement of the airway gas Raman scattering spectra. A preferred way to solve this problem and find the concentration components is to construct a Singular Value Decomposition ("SVD") of the matrix A, and to determine a pseudo-inverse matrix $A^+$, where $c = A^+ b$. If one uses this technique to determine the pseudo-inverse matrix, then one solution is $A^+ = (A^{tr}A)^{-1}A$, where $A^{tr}$ is the transpose of the matrix A, which is not necessarily square. Alternatively, one can construct a pseudo-inverse matrix $A^+$ using a least squares singular value decomposition ("SVD") approach.

Construction of a least squares SVD pseudo-inverse of a matrix A is discussed by G. Strang, *Linear Algebra And Its Applications*, Academic Press, 1980, pp. 137–145, which is incorporated by reference herein. For an $m \times n$ matrix A, the equation $Ac = b$ may be an overdetermined system of equations because the number of spectra measurements (m) often exceeds the assumed number of distinct molecules (n), each of which is assumed to correspond to a linearly independent spectral measurement in the vector space spanned by all such measurement values. The optimal choice of solution $c = c$ minimizes the length $\Vert Ac - b \Vert$ of the error vector, and one form of the solution is $c = (A^{tr}A)^{-1}A^{tr}b$. This projects the forcing function vector b into the sub-vector space spanned by the column vectors of the matrix A. The term Singular Value Decomposition refers to the decomposition of the matrix A into the form $$A = Q_1 \Sigma Q_2, \qquad (3)$$

where $Q_1$ and $Q_2$ are $m \times m$ and $n \times n$ orthogonal matrices, respectively, and $\Sigma$ is an $m \times n$ diagonal matrix with a sequence of positive diagonal entries, followed by a sequence of zero-valued diagonal entries. The diagonal entries of the matrix $\Sigma$ are determined by solving an eigenvalue problem, applied to $A^{tr}A$, and the matrices $Q_1$ and $Q_2$ are then determined by a Gram-Schmidt orthonormalization process. The SVD process is known, but its application to the spectral measurement versus concentration problem appears new.

Advantages of This Embodiment Include the Following

1. All concentration of the components of the gas mixture are determined at a single time and from the same gas sample;

2. The sample volume can be potentially quite small and is determined by the volumes of the waveguide, resonant cavity, or confocal cavity;

3. The system has a small number of parts and no moving parts—one set of imaging optics, one diffraction grating, and one photodiode array;

4. The aperture of the waveguide or cavity is small, and use of multiple slits increases the illumination in the spectrometer;

5. Measurement of the entire spectrum of the mixture increases the total optical signal, produces a better signal-to-noise ratio, and provides extra information for more accurate calculation of the concentrations; and 6. The algorithm used for solution is robust and allows construction of a pseudoinverse matrix from basis functions that represent mixtures of components and that may even contain some noise and other background signals.

Figure 4:
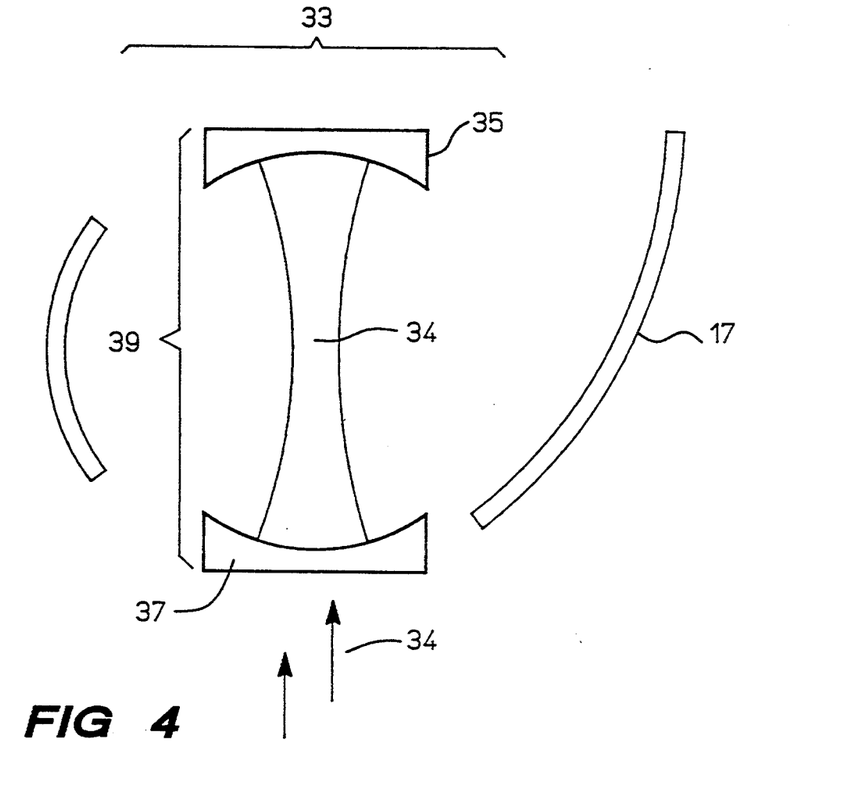
FIGS. 4 and 5 are schematic views illustrating details of light illumination apparatus for the gas samples held in the sample cells.

Another embodiment 31, shown in FIG. 4, uses the same collection optics 17 and grating spectrometer 27 as described above, but replaces the waveguide (13 in FIG. 1) with a small sample cell 33 positioned at the focal point of the first parabolic mirror 17. A laser beam 34 passes through the sample cell 33 in a direction normal to the plane of the spectrometer 25 and collection optics 17, with the polarization of the laser beam 34 being oriented normal to a line that connects the center and focal point of the parabolic mirror. Two opposed ends of the sample cell 33 can be mirrors 35 and 37 that form part of an optically resonant cavity for the laser 39, as illustrated in FIG. 4.

Figure 5:
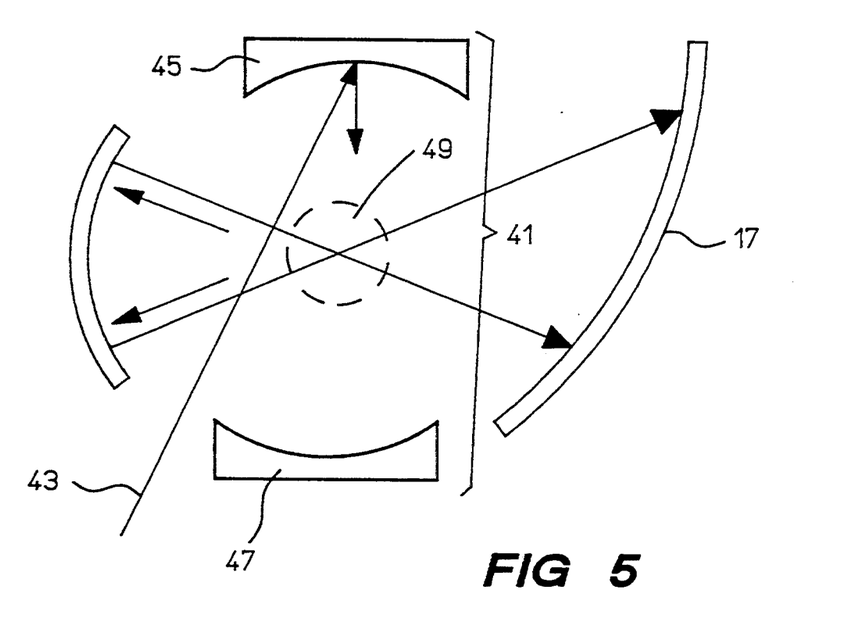

The two opposed ends of the sample cell can also be mirrors that form part of a non-resonant cavity 41, where the laser beam makes multiple reflections through a small focal region, as illustrated in FIG. 5. These embodiments have all the advantages of the embodiment shown in FIG. 4, except for the increased interaction length, and have a potentially narrow, linear scattering region that images exactly into the slit of the spectrometer. Also, this configuration may decrease the amount of unwanted scattered light into the spectrometer.

Any of the embodiments above may use multiple slits at the entrance to the spectrometer. Multiple slits cause multiple spectral images to appear on the diode array. The images are substantially identical but are translated on the array by a distance determined by the spacing of the slits. The images sum together on the array to produce a new, mixed signal. For example, if a spectrum contains a single Raman line, two slits will create two line images, spaced apart, on the detector array. Because these "multi-slit spectra" are still unique, they are useful basis functions that describe each gaseous component. The SVD and pseudo-inverse matrices can be determined for these new multiple slit basis functions and used to calculate concentrations of the sample gases present. One advantage of this technique is that a plurality of slits admits more light to the spectrometer, thereby increasing the optical efficiency of the system. The maximum number of slits that can be used is determined by the resolution of the spectrometer and by the patterns of the spectral lines. Slits of different widths can be combined, and the spacing between the slits can be variable.

Figure 6:
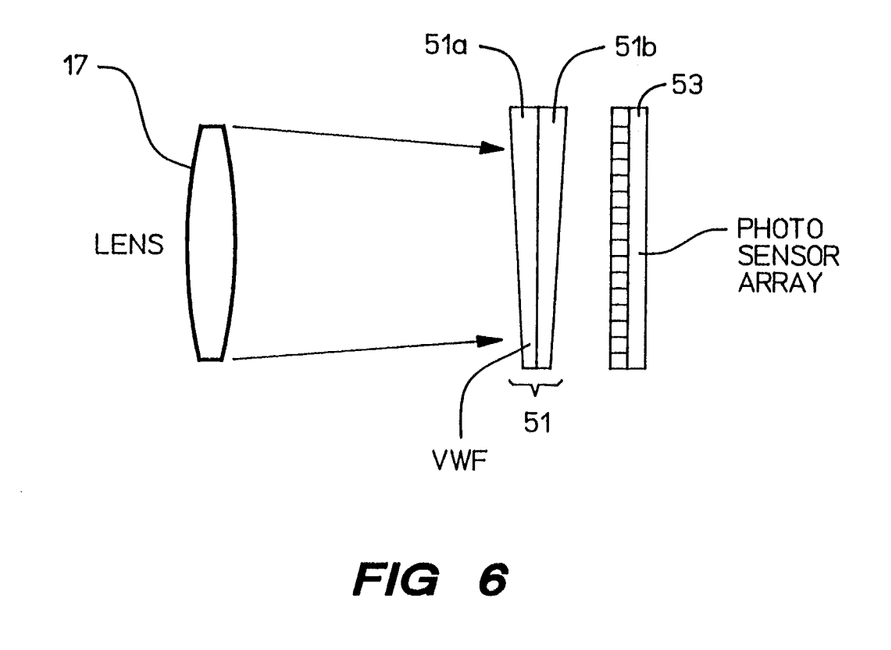
FIG. 6 is a schematic view illustrating use of a variable wavelength filter to implement the invention.

Another embodiment, illustrated in FIG. 6, replaces the grating spectrometer 27 with a variable wavelength filter ("VWF") 51 placed over or adjacent to a photosensor array 53. The collection optics 17 would direct the Raman scattered light onto the VWF and photosensor array combination for wavelength dispersal and sensing. The VWF is disclosed in another patent application, U.S. Ser. No. 07/480,172, filed on an invention by Kent Vincent and assigned to the assignee of this patent application. The VWF 51 is constructed so that the central wavelength of the narrow pass band of the filter varies linearly or strictly monotonically along the length of the VWF Each of the elements of the photosensor array detects only a narrow band of wavelengths, determined by the position that the transmitted or reflected light issues from the VWF 51. Such a VWF can be made today with band pass intervals of approximately 0.5–1.0 percent of the central wavelength. A VWF 51 may include a narrow band wavelength filter 51a and a broad band wavelength filter 51b, positioned in tandem as shown in FIG. 4. The group of light wavelengths issued (transmitted or reflected) by the narrow band filter 5 la at any point on this filter is quite narrow, as narrow as 2 nm, and the central frequency for this pass band increases monotonically, either continuously or discontinuously, as the position of the point is displaced in a selected coordinate direction (x) along the falter. The wide band filter 51b has a somewhat wider wavelength pass band at any point on this filter. The central frequency of this wide band filter approximately coincides with the central frequency of the narrow band filter 51a at any corresponding coordinate x for these two filters. The pass band of the wide band filter cuts off all light wavelengths for which the narrow band filter 51a would manifest unwanted side band emission so that the combination of the narrow band light filter 51a and the wide band light filter 51b produces a narrow wavelength band of light with no side band emissions; and the central frequency of this narrow band increases (or decreases) monotonically with increase of the coordinate x.

In the foregoing embodiments, the sample cell or waveguide tube 13 shown in FIG. 1 has been illustrated as a long cylindrical waveguide tube, coated on its interior or exterior surface with a highly reflecting material that reflects the Raman-scattered light and directs the scattered light along the waveguide. In another preferred embodiment 61, shown in FIG. 7, a cylindrical tube 63 is again coated on its interior or exterior surface with a highly reflecting material 65, but a small aperture 67 is formed in this material at a position near the center of the length of the tube 63. Raman-scattered light is emitted from the interior of the waveguide tube 63, and this radiation is received and analyzed by collection optics, a spectrometer and a light sensor array as illustrated in FIG. 1 .Because the remainder of the light-receiving surfaces of the waveguide tube 63, excepting the aperture 67, are highly reflecting at the scattered wavelength $\lambda = \lambda_R$, the waveguide arrangement shown in FIG. 7 will repeatedly scatter light emitted on or adjacent to the longitudinal axis LL' back into the region near the axis LL' after reflection from the tube walls. This always occurs when light scatters from an interaction region that is coincident with a narrow light beam travelling along the axis in a reflecting tube. Any region near the tube axis contains multiple images of light scattering regions positioned along or adjacent to the tube axis. A light beam collected from this region through the aperture 67 has a greater intensity than light emitted from a point along the tube axis, in the absence of a reflecting waveguide or coating 65. Light that is ultimately emitted through the aperture 67 contains: (1) the direct image of light scattered from the region adjacent to and along the tube axis; (2) reflections of these direct images from the tube wall opposite the aperture 67; and (3) light from images of multiple reflections along the entire length of the tube axis. The imaging properties of the waveguide 63 are improved if the maximum diameter of the light beam in travelling in the waveguide is made as small as possible, relative to the inside diameter of the waveguide tube.

Figure 7:
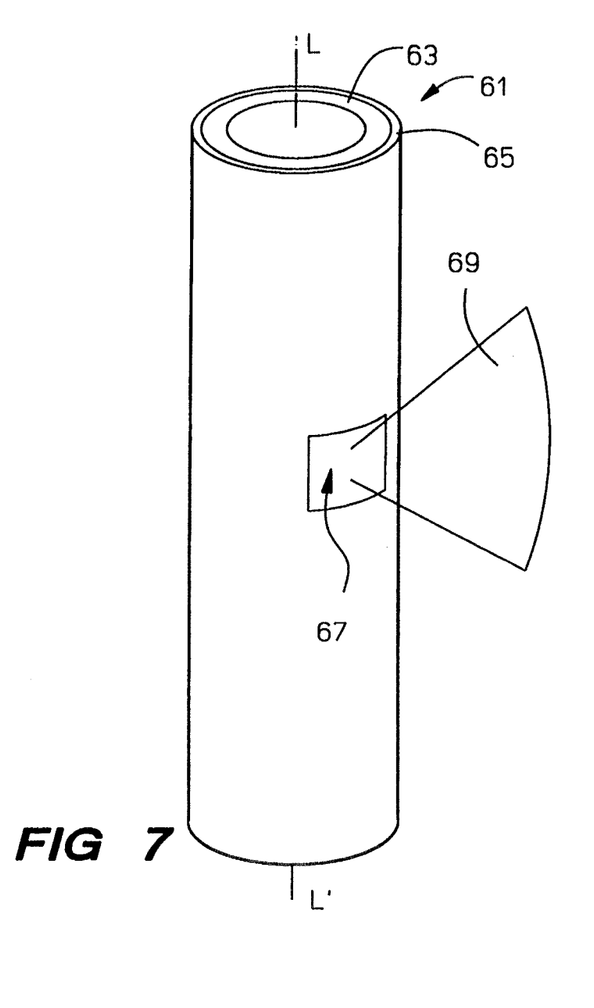
FIGS. 7, 8, 9 and 10 are schematic views illustrating use of light-emitting apertures with tubular sample cells according to other embodiments of the invention.

The aperture 67 in FIG. 7 is formed by removing, or by not initially applying, the reflective coating 65 in the aperture region. The aperture itself can have any shape, although circular or elliptical shapes may be preferable for subsequent collection by circular collection optics of the light emitted from the aperture. The shape and size of the aperture will preferably be determined by the requirements of the external optical system. If collection optics are used, the aperture diameter $d_{aperture}$ might be chosen to satisfy the relation $d_{tube}/2 < d_{aperture} < d_{tube}$, where $d_{tube}$ is the tube inside diameter. For improved performance, the aperture 67 is placed at or adjacent to the center of the tube axis, and the length L of the tube should satisfy $L/d_{tube} > 20$.

Figure 8:
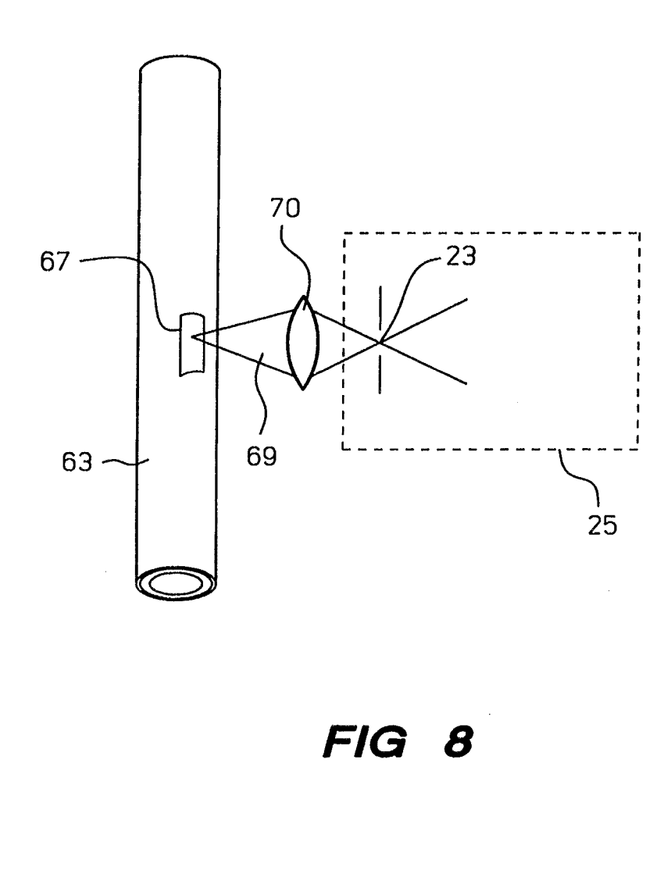

FIG. 8 illustrates use of the tube 63, with the small aperture 67 therein, in this alternative preferred embodiment of the invention. The light beam 69 that issues from the aperture 67 is collected by collection optics 70 and focused on the entrance slit 23 of the spectrometer 25 that is constructed and operated as shown in FIG. 1. Processing of the light beam 69 after the beam has passed through the spectrometer entrance slit 23 occurs as discussed in connection with the spectrometer 25 shown in FIG. 1.

Figure 9:
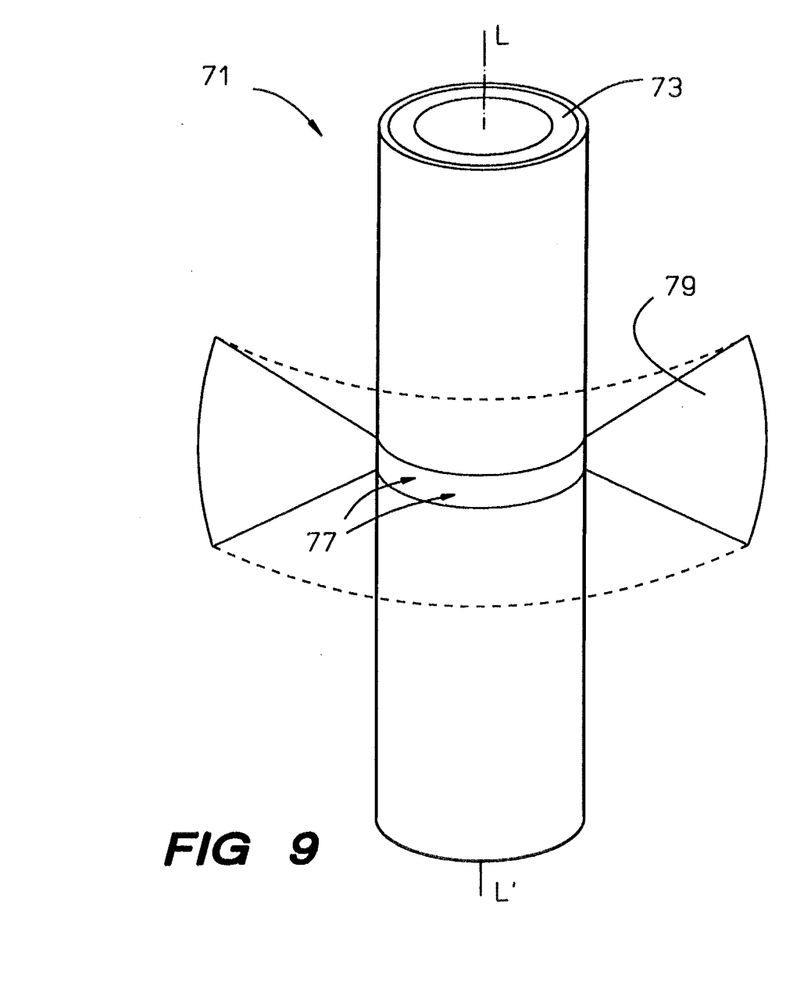

In another embodiment 71, shown in FIG. 9, the small single aperture 67 in FIG. 7 is replaced by a radial band aperture 77 on a waveguide tube 73 from which a Raman-scattered light beam 79 is emitted. Processing of the light beam 79 is similar to processing of the light beam 69 in FIG. 8.

Figure 10:
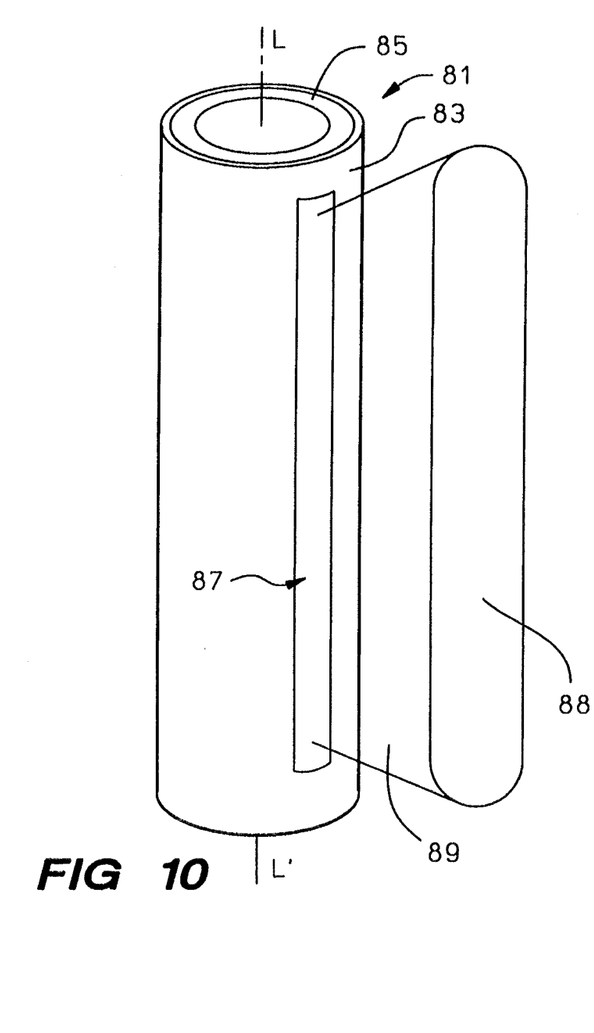

In another embodiment 81, shown in FIG. 10, the small aperture 67 in FIG. 7 is replaced by a narrow, longitudinally oriented aperture 87 on a waveguide tube 83 from which a Raman-scattered light beam 89 is emitted. Collection optics 88 preferably surrounds the tube 83 and collects substantially all the light beam 89 emitted from the longitudinally oriented aperture 87. Subsequent processing of the light beam 89 is similar to processing of the light beam 69 in FIG. 8.

We claim:

1. An apparatus for determining a spectral signature of an unknown gas in a single measurement comprising:

a reflective tube, having an aperture and a highly reflective surface, receiving and holding the unknown gas;

a light beam at a selected wavelength illuminating the unknown gas to produce Raman scattered light that is indicative of the spectral signature, wherein a first and a second portion of the Raman scattered light exits through the aperture and a third portion remains in the reflective tube;

wherein the first portion includes Raman scattered light originating from a collection region which is proximate to the aperture and the second portion includes Raman scattered light originating from outside the collection region;

the surface reflecting the second portion of the Raman scattered light such that the second portion is redirected and exits through the aperture;

a spectrometer, receiving the Raman scattered light that exits the aperture, dispersing the received Raman scattered light according to spectral wavelengths; and an array of photodetectors, each photodetector corresponding to one of the spectral wavelengths, each photodetector detecting the dispersed Raman scattered light and producing an output signal at a strength proportional to [the concentration of]the detected dispersed Raman scattered light;

wherein the spectral signature corresponding to the strength of the output signals identifies and quantifies the unknown gas.

2. The apparatus, as defined in claim 1, the selected wavelength being between 500 nm and 850 nm, inclusively.

3. The apparatus, as defined in claim 1, the reflective tube further including two opposing ends, wherein the aperture of the reflective tube is a region in one of the two opposing ends, the aperture being transparent to the Raman scattered light.

4. The apparatus, as defined in claim 1, wherein the aperture is a region of the reflective tube that is transparent to Raman scattered light so that the first and second portions of Raman scattered light exits through the aperture.

5. The apparatus, as defined in claim 1, wherein the aperture is a partial circumferential band on the reflective tube that is transparent to Raman scattered light so that the first and second portions of Raman scattered light exits through the aperture.

6. The apparatus, as defined in claim 1, wherein the aperture is a narrow, longitudinally oriented band on the reflective tube that is transparent to Raman scattered light so that the first and second portions of Raman scattered light exits through the aperture.

* * * * *